(12) United States Patent
Nishigishi

(10) Patent No.: US 10,744,008 B2
(45) Date of Patent: Aug. 18, 2020

(54) STENT

(71) Applicant: PENTAS Inc., Tokyo (JP)

(72) Inventor: Makoto Nishigishi, Tokyo (JP)

(73) Assignee: PENTAS Inc., Tokyo (JP)

( * ) Notice: Subject to any disclaimer, the term of this patent is extended or adjusted under 35 U.S.C. 154(b) by 81 days.

(21) Appl. No.: 16/075,344

(22) PCT Filed: Feb. 9, 2017

(86) PCT No.: PCT/JP2017/004703
§ 371 (c)(1),
(2) Date: Aug. 3, 2018

(87) PCT Pub. No.: WO2017/141805
PCT Pub. Date: Aug. 24, 2017

(65) Prior Publication Data
US 2019/0053923 A1    Feb. 21, 2019

(30) Foreign Application Priority Data
Feb. 16, 2016 (JP) ................ 2016-026809

(51) Int. Cl.
*A61F 2/88* (2006.01)
*A61F 2/90* (2013.01)
*A61F 2/00* (2006.01)

(52) U.S. Cl.
CPC ............ *A61F 2/88* (2013.01); *A61F 2/90* (2013.01); *A61F 2/0095* (2013.01); *A61F 2230/0071* (2013.01); *A61F 2240/001* (2013.01)

(58) Field of Classification Search
CPC ..................... A61F 2/06; A61F 2/88
USPC ................... 623/1.15, 1.5–1.53
See application file for complete search history.

(56) References Cited

U.S. PATENT DOCUMENTS

| | | | |
|---|---|---|---|
| 9,039,754 B2* | 5/2015 | Nishigishi | A61F 2/90 623/1.22 |
| 10,470,902 B2* | 11/2019 | Sheldon | A61F 2/06 |
| 2010/0076543 A1 | 3/2010 | Melsheimer | |
| 2012/0265294 A1 | 10/2012 | Nishigishi | |
| 2013/0066415 A1 | 3/2013 | Hocking | |
| 2013/0204350 A1* | 8/2013 | Richter | A61L 31/022 623/1.16 |
| 2013/0211492 A1 | 8/2013 | Schneider | |
| 2013/0282108 A1* | 10/2013 | Houston | A61F 2/06 623/1.22 |
| 2015/0257908 A1 | 9/2015 | Chao | |
| 2016/0143754 A1* | 5/2016 | Orion | A61F 2/82 623/1.15 |

(Continued)

FOREIGN PATENT DOCUMENTS

| | | | |
|---|---|---|---|
| JP | 2011244926 A | 12/2011 | |
| JP | 2012501726 A | 1/2012 | |

(Continued)

OTHER PUBLICATIONS

International Search Report dated May 9, 2017 filed in PCT/JP2017/004703.

*Primary Examiner* — Suzette J Gherbi
(74) *Attorney, Agent, or Firm* — Rankin, Hill & Clark LLP

(57) ABSTRACT

A tip end portion of a strand forming a stent is rounded off. In a stent 10 formed by helicoidally braiding a plurality of strands 20, the tip end portion of each of the strands 20 is rounded off.

7 Claims, 3 Drawing Sheets

(56) References Cited

U.S. PATENT DOCUMENTS

| | | | |
|---|---|---|---|
| 2016/0175085 A1* | 6/2016 | Johnson | A61F 2/01 606/200 |
| 2018/0271682 A1* | 9/2018 | Treacy | A61F 2/88 |
| 2018/0272044 A1* | 9/2018 | Hossainy | A61F 2/88 |
| 2019/0046340 A1* | 2/2019 | Nishigishi | A61F 2/88 |
| 2019/0133800 A1* | 5/2019 | Krolik | A61F 2/91 |
| 2019/0201218 A1* | 7/2019 | Shobayashi | A61F 2/89 |
| 2019/0262151 A1* | 8/2019 | Treacy | A61F 2/90 |
| 2019/0365548 A1* | 12/2019 | Sirhan | A61F 2/915 |

FOREIGN PATENT DOCUMENTS

| | | |
|---|---|---|
| JP | 2012223209 A | 11/2012 |
| JP | 2013541358 A | 11/2013 |
| WO | 2015138763 A1 | 9/2015 |

\* cited by examiner (A)

(B)

STENT

TECHNICAL FIELD

The present invention relates to a stent.

BACKGROUND ART

There is known a stent for medical purpose as follows. The stent is formed by helicoidally braiding a plurality of strands (see Patent Literature 1).

CITATION LIST

Patent Literature

Patent Literature 1: JP 2012-223209 A

SUMMARY OF INVENTION

Technical Problem

In recent years, a stent formed by helicoidally braiding a plurality of strands is used for the purpose of medical treatment of an aneurysm. A metal wire is generally used in the strand which forms the stent. However, there is a concern that a tip end of the strand may damage the inside of a blood vessel when the stent is implanted in the blood vessel, or the strand may damage the inside of a catheter when the stent moves in the catheter. Therefore, there are needed studies to prevent the tip end of the strand from damaging the blood vessel or the catheter. However, the related art has failed to consider such a technology.

Solution to Problem

According to a first aspect of the invention, the stent is formed by helicoidally braiding a plurality of strands, and a tip end portion of each of the strands is rounded off.

According to a second aspect of the invention, in the stent of the first aspect, the tip end portion of the strand is irradiated with a laser beam to form the tip end portion of the strand in an approximate spherical shape to round off the tip end portion of the strand.

According to a third aspect of the invention, in the stent of the second aspect, the tip end portion of the strand is formed in an approximate spherical shape such that a diameter of the stent before expanding becomes a diameter to be stored in an inner diameter of a tube or a catheter for storing the stent.

Advantageous Effects of Invention

According to the invention, a tip end portion of each of a plurality of strands of a stent is rounded off, so that it is possible to prevent that the tip end of the strand damages on the inside of a blood vessel, and damages the inside of a catheter.

DESCRIPTION OF EMBODIMENTS

Figure 1:
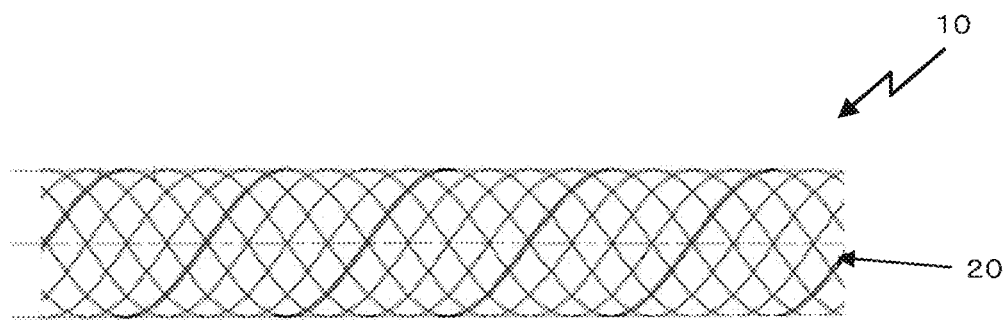
FIG. 1 is a diagram schematically illustrating a shape of a stent formed by helicoidally braiding a plurality of strands.

FIG. 1 is a diagram schematically illustrating a shape of a stent in the embodiment. In the embodiment, a stent 10 is assumed to be formed by helicoidally braiding a plurality of strands 20 as illustrated in FIG. 1. In the strand 20, for example, a metal material such as stainless steel, Co—Cr alloy (cobalt-chromium alloy), and Ni—Ti alloy (nickel-titanium alloy) is used.

The stent 10 is formed by helicoidally braiding the plurality of metal strands 20. There are a plurality of stent types different in the number of strands 20 of the stent 10 and a strand diameter. Examples of the stent type include five types as follows.

(Stent Type 1) 16-2.5 mm
A 16-2.5 mm stent type is formed by braiding 16 strands with each other, in the type, the strand diameter of each strand is 42 μm, and a blood vessel having a blood vessel diameter of 2.5 mm±5 mm becomes an implantation target. In addition, an inner diameter of a storage tube for storing such type of stent before use, and an inner diameter of a catheter for using such type of stent are 0.55 mm.

(Stent Type 2) 4-3.0 mm
A 24-3.0 mm stent type is formed by braiding 24 strands with each other. In the type, the strand diameter of each strand is 42 μm, and a blood vessel having a blood vessel diameter of 3.0 mm±5 mm becomes an implantation target. In addition, an inner diameter of a storage tube for storing such type of stein before use, and an inner diameter of a catheter for using such type of stent are 0.55 mm.

(Stent Type 3) 24-4.0 mm
A 24-4.0 mm stent type is formed by braiding 24 strands with each other. In the type, the strand diameter of each strand is 42 μm, and a blood vessel having a blood vessel diameter of 4.0 mm±5 mm becomes an implantation target. In addition, an inner diameter of a storage tube for storing such type of stent before use, and an inner diameter of a catheter for using such type of stent are 0.55 mm.

(Stent Type 4) 32-4.0 mm
A 32-4.0 mm stent type is formed by braiding 32 strands with each other. In the type, the strand diameter of each strand is 42 μm, and a blood vessel having a blood vessel diameter of 4.0 min±5 mm becomes an implantation target. In addition, an inner diameter of a storage tube for storing such type of stent before use, and an inner diameter of a catheter for using such type of stent are 0.59 mm.

(Stent Type 5) 32-5.0 mm
A 32-5.0 mm stent type is formed by braiding 32 strands with each other. In the type, the strand diameter of each strand is 50 μm, and a blood vessel having a blood vessel diameter of 5.0 mm±5 mm becomes an implantation target. In addition, an inner diameter of a storage tube for storing such type of stent before use, and an inner diameter of a catheter for using such type of stent are 0.59 mm.

In the stent 10 formed by helicoidally braiding the plurality of metal strands 20, there are tip end portions of the strand 20 at both ends of the stent 10. In general, the cross section of the tip end portion is substantially flat as illustrated in FIG. 2(A), and the cross section has a corner portion. In this case, the inside of the blood vessel may be damaged by a tip end portion 2a of the strand 20 of the stent when the stent 10 is implanted in a blood vessel. When the stent 10 moves in the catheter, there is a concern that the inside of the catheter is damaged or cut. In the embodiment, the tip end portion of the strand 20 is rounded off as illustrated in FIG. 2(b) in order to prevent such a concern. With this configuration, a tip end portion 2b of the strand 20 has no corner portion which may cause a damage on the inside of the blood vessel and the inside of the catheter.

A method of making the tip end portion of the strand 20 rounded off is not particularly limited. For example, the tip end portion of the strand 20 may be rounded off by irradiating, the tip end portion of the strand 20 with a laser beam to make the tip end portion of the strand 20 into a spherical shape as illustrated in FIG. 2(b). Further, the shape of the tip end portion of the strand 20 may be not necessarily an exact spherical shape. The object of the invention can be achieved as long as the shape is almost spherical shape without a corner portion.

Figure 2:
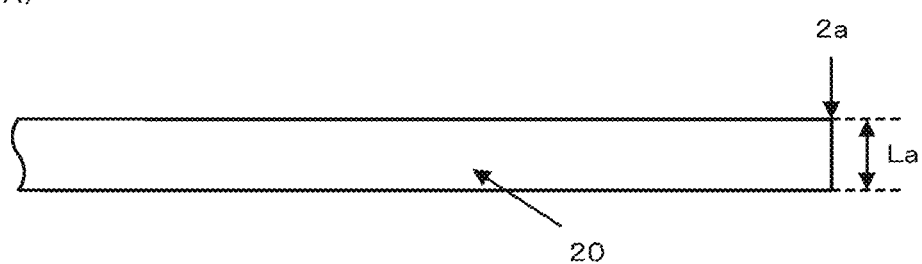
FIG. 2 is a diagram schematically illustrating an example in a case where the tip end of the strand is rounded off.
Figure 2:
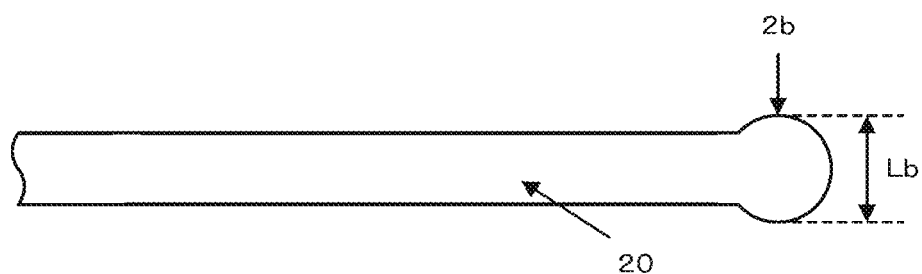

When the rounding is performed to make the strand 20 have almost the spherical tip end portion, the diameter of the tip end portion of the strand is necessarily adjusted such that the stent 10 is stored in the storage tube or the catheter. For example, considering the 24-4.0 mm stent type, the inner diameter of the storage tube and the inner diameter of the catheter are 0.55 mm. Therefore, when the diameter of the tip end portion of the stent 10 exceeds 0.55 mm by rounding off the tip end portion of the strand 20, the stent 10 is not possible to be stored in the storage tube and the catheter. In order to prevent such a problem, when the strand 20 is rounded off, the tip end portion of the strand 20 is necessarily formed in an approximate spherical shape such that the diameter of the stent before expanding falls within the inner diameter of the tube or the catheter for storing the stent. Experimentally, if a diameter Lb of the tip end portion of the strand after rounding off as illustrated in FIG. 2 is set to be about 1 to 1.5 times a diameter La of the tip end portion of the strand before rounding off, the stent 10 formed by braiding the strands 20 is made to have a diameter which falls within the inner diameter of the tube or the catheter for storing the stent.

Figure 3:
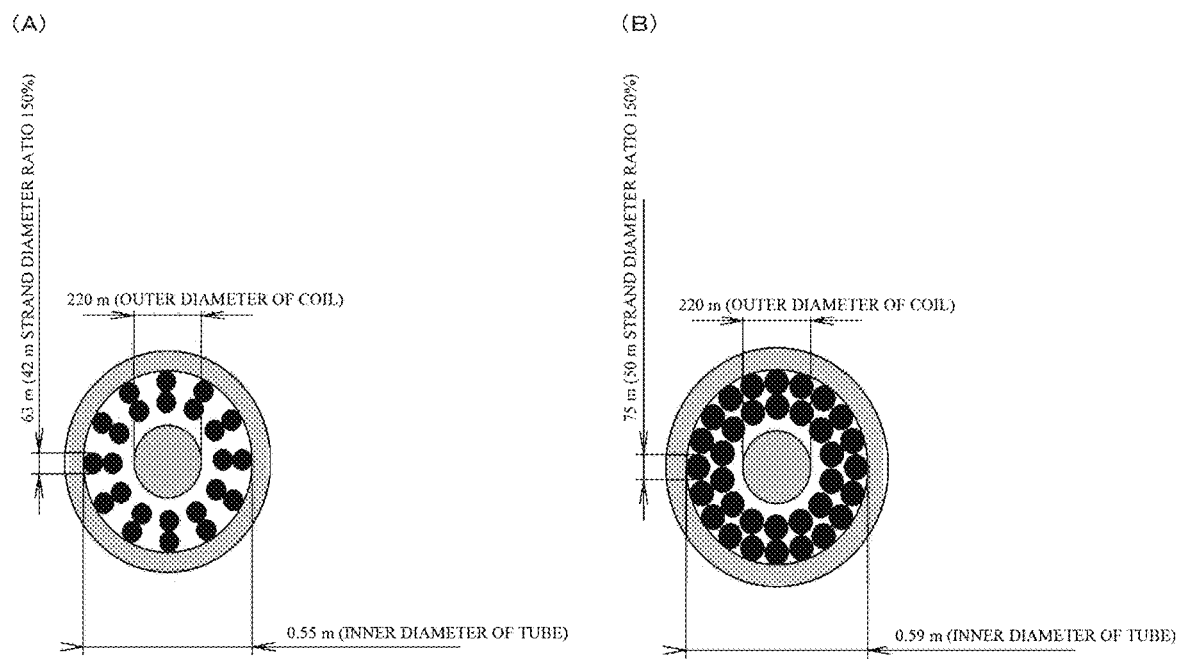
FIG. 3 is a diagram schematically illustrating a state in which the stent having a rounded strand is stored in a storage tube.

FIG. 3 is a diagram schematically illustrating a state where the stent having the rounded tip end of the strand is stored in a storage tube. FIG. 3(A) schematically illustrates a state where the 24-4.0 mm stent having the rounded tip end portion of the strand is stored in the storage tube of an inner diameter of 0.55 mm. As illustrated in FIG. 3(A), a coil passes through the inner portion of the stent to fix the tip end of the stent, and the outer diameter of the coil is 220 μm. FIG. 3(A) illustrates a case where the tip end portion of the strand of a diameter of 42 μm is rounded off to be 63 μm which corresponds to 1.5 times (150%) the diameter of the tip end. According to a simulation result illustrated in FIG. 3(A), it can be seen that the stent stored in the storage tube even when the strand is rounded off such that the diameter of the tip end of the 24-4.0 mm stent is 1.5 times the diameter of the strand.

FIG. 3(B) schematically illustrates a state where the 32-5.0 mm stent having the rounded tip end portion of the strand is stored in the storage tube of an inner diameter of 0.59 mm. As illustrated in FIG. 3(B), a coil passes through the inner portion of the stent to fix the tip end of the stent, and the outer diameter of the coil is 220 μm. FIG. 3(B) illustrates a case where the tip end portion of the strand of a diameter of 50 μm is rounded off to be 75 μm which corresponds to 1.5 times (150%) the diameter of the strand. According to a simulation result illustrated in FIG. 3(B), it can be seen that the stent is stored in the storage tube even when the strand is rounded off such that the diameter of the tip end of the 32-5.0 mm stent is 1.5 times the diameter of the strand. Further, FIG. 3 has illustrated an example where the stents stored in the storage tube even after rounding off, and the invention may also be applied to the catheter having a similar inner diameter.

According to the embodiment, the following operational effects can be obtained.

(1) In the stent formed by helicoidally braiding the plurality of strands, the tip end portion of each strand is rounded off. With this configuration, it is possible to prevent a case where the blood vessel is damaged when the stent is implanted in the blood vessel and a case where the catheter is damaged or cut when the stent moves in the catheter.

(2) The tip end portion of the strand has been rounded off by irradiating the tip end portion of the strand with a laser beam to form the tip end portion of strand in an approximate spherical shape. With this configuration, it is possible to form the cross section of the tip end portion of the strand in a curved shape having no corner portion. In addition, it is possible to save trouble such as cutting and polishing by using the laser beam.

(3) The tip end portion of the strand has been formed in an approximate spherical shape such that the diameter of the stent before expanding falls within the inner diameter of the tube or the catheter for storing the stent. With this configuration, even in a case where the tip end of the strand is rounded off, the stent can be stored in the storage tube or the catheter which is fixed in size.

Modifications

Further, the stent of the embodiment may be modified as follows.

(1) In the embodiment, five types of the stents have been exemplified, but the stent types are not limited thereto.

(2) In the embodiment, the description has been given about an example in which the diameter of the stent formed by braiding the strands falls within the inner diameter of the tube or the catheter for storing the stent if the diameter 2b of the tip end portion of the strand after rounding off as illustrated in FIG. 2 is set to be about 1 to 1.5 times the diameter of the tip end portion of the strand before rounding off. However, the diameter of the tip end portion of the strand is not limited to a range of 1 to 1.5 times the diameter before rounding off as long as the diameter of the stent falls within a range that the stent is stored in the inner diameter of the tube or the catheter for storing the stent.

Further, the invention is not limited to any one of the configurations of the above-described embodiment as long as the characteristic functions of the invention are not degraded. In addition, the above-described embodiment and a plurality of modifications may be combined.

Priority is claimed on Japanese Patent Application No. 2016-26809 filed on Feb. 16, 2016, the content of which is incorporated herein by reference.

REFERENCE SIGNS LIST 10 stent
20 strand

The invention claimed is:

1. A stent which is formed by helicoidally braiding a plurality of strands,
  wherein a tip end portion of each of the strands is rounded off, and
  a diameter of the tip end portion after rounding off is 1 to 1.5 times a diameter of the tip end portion before rounding off.

2. The stent according to claim 1,
wherein the tip end portion of the strand is irradiated with a laser beam to form the tip end portion of the strand in an approximate spherical shape to round off the tip end portion of the strand.

3. The stent according to claim 2,
wherein the tip end portion of the strand is formed in an approximate spherical shape such that a diameter of the stent before expanding falls within a diameter to be stored in an inner diameter of a tube or a catheter for storing the stent.

4. The stent according to claim 1,
wherein the stent comprises a coil passing through an inner portion of the stent to fix a tip end of the stent.

5. A stent stored in a storage tube, comprising:
a plurality of strands being helicoidally braided; and
the storage tube storing the plurality of strands,
wherein a tip end portion of each of the strands is rounded off, and
the tip end portion of the strand has an approximate spherical shape such that a diameter of the stent before expanding falls within a diameter to be stored in an inner diameter of the storage tube.

6. The stent stored in the storage tube according to claim 5,
wherein a diameter of the tip end portion after rounding off is 1 to 1.5 times a diameter of the tip end portion before rounding off.

7. The stent stored in the storage tube according to claim 5, further comprising a coil passing through an inner portion of the stent to fix a tip end of the stent.

* * * * *